United States Patent [19]
Schönafinger et al.

[11] Patent Number: 4,610,984
[45] Date of Patent: Sep. 9, 1986

[54] SUBSTITUTED PIPERAZIN-1-YL-ACETIC ACID AMIDES

[75] Inventors: Karl Schönafinger, Alzenau; Rudi Beyerle, Frankfurt am Main; Ursula Schindler, Mörfelden-Walldorf; Piero Martorana, Bad Homburg; Rolf-Eberhard Nitz, Frankfurt am Main, all of Fed. Rep. of Germany

[73] Assignee: Cassella Aktiengesellschaft, Frankfurt(Main)-Fechenheim, Fed. Rep. of Germany

[21] Appl. No.: 601,637

[22] Filed: Apr. 18, 1984

[30] Foreign Application Priority Data

Apr. 28, 1983 [DE] Fed. Rep. of Germany ....... 3315424

[51] Int. Cl.[4] .............. A61K 31/495; C07D 295/18; C07D 295/20; C07D 409/12

[52] U.S. Cl. .................... 514/235; 514/255; 544/121; 544/357; 544/359; 544/360; 544/372; 544/379; 544/386

[58] Field of Search .............. 544/121, 359, 357, 360, 544/379, 372, 386; 514/235, 255

[56] References Cited

U.S. PATENT DOCUMENTS 4,247,549  1/1981  Ohnmacht et al. ................ 544/390

FOREIGN PATENT DOCUMENTS 64878    11/1982  European Pat. Off. ........... 544/386
2113942   6/1912  France ................................ 544/386
1324423   7/1973  United Kingdom ............... 544/386

Primary Examiner—Robert T. Bond
Attorney, Agent, or Firm—Horst M. Kasper

[57] ABSTRACT

This invention relates to certain 4-acyl-piperazine-1-acetamides. These compounds are useful as memory and learning enhancers and for the treatment and prevention of cerebral insufficiency.

9 Claims, No Drawings

SUBSTITUTED PIPERAZIN-1-YL-ACETIC ACID AMIDES

The invention relates to new substituted piperazin-1-ylacetic acid amides of the formula I

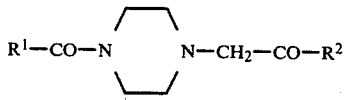
(I)

wherein $R^1$ denotes phenyl, phenyl which is substituted by one, two or three independent substituents from the group comprising $(C_1-C_4)$ alkyl, $-O-(C_1-C_4)$—alkyl, $-CO-O-(C_1-C_4)$—alkyl, $-SCH_3$, $-NH_2$, $-NH-(C_1-C_3)$—alkyl, $-N((C_1-C_2)-\text{alkyl})_2$, $-F$, $-Cl$, $-Br$, $-I$, $-OH$ and $-SH$, or pyridyl, thienyl, furyl, p-chlorophenoxymethyl, amino, alkylamino with 1 to 5 C atoms, phenylamino, phenylamino which is substituted in the phenyl nucleus by $-Cl$, $-Br$, $-CH_3$ or $-OCH_3$, or alkoxy with 1 to 4 C atoms, $R^2$ denotes amino, alkylamino with 1 to 4 C atoms, dialkylamino with 1 to 4 C atoms in each alkyl radical, morpholino, 4-methyl-piperazin-1-yl, pyrrolidin-1-yl, piperidino, cyclohexamethyleneimino, diethanolamino, dipropanolamino, $-NH(CH_2)_n-R^3$, $-NH(CH_2)_m-R^4$ or 2-($R^3$—carbonyl)-pyrrolidin-1-yl, $R^3$ denotes hydroxyl, alkoxy with 1 to 4 C atoms, amino, alkylamino with 1 to 4 C atoms or dialkylamino with 1 to 4 C atoms in each alkyl radical, $R^4$ denotes phenyl, methoxyphenyl, methylphenyl, dimethoxyphenyl, dimethylphenyl or pyridyl, n denotes 2 or 3 and m denotes 1 or 2, and their acid addition compounds.

The alkyl or alkoxy radicals represented by $R^1$, $R^2$ and $R^3$ can be straight-chain or branched, including cases where they are substituents of other radicals.

The radical $R^1$ preferably denotes phenyl, methoxyphenyl, chlorophenyl, bromophenyl, fluorophenyl, $(C_1-C_4)$-alkylphenyl, 4-chlorophenoxymethyl, dimethoxyphenyl, dichlorophenyl, methoxycarbonylphenyl, acetoxy-methoxyphenyl, $(C_1-C_2)$-alkoxy, amino, chlorophenylamino, trimethoxyphenyl, thienyl, pyridyl or furyl.

The abovementioned preferred substituted phenyl radicals represented by $R^1$ are preferably monosubstituted in the 3-position or, in particular, 4-position or preferably disubstituted in the 3,4-position or preferably trisubstituted in the 3,4,5-position. A pyridyl radical is preferably a 3-pyridyl radical. A furyl radical is preferably a 2-furyl radical. A thienyl radical is preferably a 2-thienyl radical. The radical $R^2$ preferably denotes amino, $(C_1-C_4)$-alkylamino, di-$(C_1-C_4)$ -alkylamino, morpholino, 4-methyl piperazin-1-yl, pyrrolidin-1-yl, piperidino, diethanolamino, $-NH(CH_2)_n-R^3$, $-NH(CH_2)_m-R^4$ or 2-($R^3$—carbonyl)-pyrrolidin-1-yl, wherein $R^3$ and $R^4$ preferably have the following meanings: $R^3$: hydroxyl, alkoxy with 1 or 2 C atoms, amino, alkylamino with 1 or 2 C atoms or dialkylamino with 1 or 2 C atoms in each alkyl radical and $R^4$: phenyl, methoxyphenyl, dimethoxyphenyl or pyridyl.

Very particularly preferably, $R^1$ denotes 4-methoxyphenyl and $R^2$ denotes morpholino.

The compounds of the formula I are prepared by a process in which (a) a piperazin-1-yl-acetic acid amide of the formula II

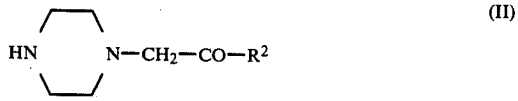
(II)

is reacted with an acylating agent III, which introduces the acyl radical $R^1$—CO— into the compound II. In the case where the radical $R^1$ is bonded to the carbonyl group of compound I via a carbon atom, suitable acylating agents are: carboxylic acid halides, in particular carboxylic acid chlorides, carboxylic acid anhydrides, carboxylic acid esters and carboxylic acids of the formula IIIa

(IIIa)

wherein X denotes halogen, $-O-CO-R^1$, $-O$—alkyl or $-OH$. In the case where the radical $R^1$ is bonded to the carbonyl group of the compound I via a nitrogen atom, isocyanic acid esters or isocyanic acid of the formula IIIb

(IIIb)

are suitable acylating agents. In the formula IIIb, the meaning of the radical $R^5$ is chosen so that the radical ($R^5$—NH—) is identical to the radical $R^1$ representing amino, alkylamino with 1 to 5 C atoms, phenylamino or phenylamino which is substituted in the phenyl nucleus by $-Cl$, $-Br$, $-CH_3$ or $-OCH_3$. $R^5$ can accordingly denote hydrogen, $(C_1-C_5)$—alkyl, phenyl or phenyl which is substituted by $-Cl$, $-Br$, $-CH_3$ or $-OCH_3$. In the case where the radical $R^1$ is bonded to the carbonyl group of the compound I via an oxygen atom, chloroformic acid esters, for example, of the formula IIIc

(IIIc)

are suitable as acylating agents. Alternatively, the compounds of the formula I are prepared by a process in which (b) a piperazide of the formula IV is reacted with a compound of the formula V

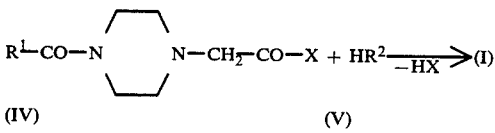

wherein Y denotes halogen, in particular Cl, $-OSO_2CH_3$, $-OSO_2$—phenyl or O—tosyl, or in which (c) a piperazin-1-yl-acetic acid derivative of the formula VI is reacted with an amine of the formula VII

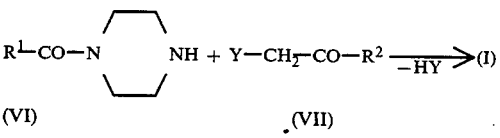

wherein X has the meanings given for process (a). X preferably denotes Cl or $-O-(C_1-C_4)$—alkyl in processes (a) and (c). In the compounds II to VI, the radicals $R^1$ and $R^2$ have the meanings already mentioned at the outset.

Processes (a) to (c) are familiar chemical process steps. Processes (a) to (c) are preferably carried out in a suitable inert solvent. Examples of suitable solvents are alcohols, preferably for reaction (b), and in particular those with 1 to 6 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8 C atoms in the molecule, such as, for example diethyl ether, methylethyl ether, di-n-propyl ether, di-iso-propyl ether, methyl n-butyl ether, ethyl propyl ether, di-n-butyl ether, tetrahydrofuran, 1,4-dioxane, 1,2-dimethoxyethane and bis-β-methoxyethyl ether; polyethers, such as, for example, polyethylene glycols with a molecular weight of up to about 600; oligoethylene glycol dimethyl ethers, such as, for example, pentaglyme; glycols and partially etherified glycols, such as, for example, ethylene glycol, propylene glycol, trimethylene glycol, ethylene glycol monomethyl ether, ethylene glycol monoethyl ether and diethylene glycol monoethyl ether; ketones, in particular those with 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, benzophenone and acetophenone; aliphatic hydrocarbons, such as, for example, low-boiling and high-boiling petroleum ethers; aromatic hydrocarbons, such as, for example, benzene, toluene, o-, m- and p-xylene and pyridine; halogenated aliphatic or aromatic hydrocarbons, such as, for example, methylene chloride, chloroform, carbon tetrachloride, ethylene chloride, chlorobenzene and dichlorobenzene; nitriles, such as, for example, acetonitrile; amides, such as, for example, dimethylformamide and N-methyl-pyrrolidone; hexamethylphosphoric acid triamide; sulphoxides, such as, for example, dimethylsulphoxide; and water. Mixtures of various solvents can also be used.

In all the process steps, the reaction is as a rule carried out at room temperature. However, depending on the reactivity of the reactants, it may be advantageous to carry out the reaction with cooling at lower temperatures or at elevated temperature, for example up to the reflux temperature of the solvent or solvent mixture used. In many cases, the reaction temperature is $-10°$ C. to 25° C., preferably 0° C. to 20° C.

In respect of a high rate of reaction and a high yield, it is as a rule also advantageous additionally to use a base as an acid-trapping agent in reactions (a) to (c), in which hydrogen chloride is split off as HX or HY. Examples of suitable bases of this type are: alkali metal carbonates, such as sodium carbonate or potassium carbonate, alkali metal bicarbonates, such as $NaHCO_3$, or organic amines, in particular tertiary organic amines, such as pyridine, or tertiary aliphatic amines with 3 to 9 C atoms, such as trimethylamine, triethylamine or tri-n-propylamine.

If water is split off in reactions (a) and (c), it is advantageous to carry out the reaction in an anhydrous medium and expedient to add a water-trapping agent. Examples of suitable water-trapping agents are carbodiimides, such as dicyclohexylcarbodiimide.

In the preparation of the compounds of the formula I by process steps (a) to (c), the starting components are usually employed in approximately equimolar amounts. If a starting amine is also to act as the acid-trapping agent, the amine is employed in excess. This excess can be, for example, up to a 10 molar excess or even more. The batches are worked up by customary processes.

The starting substances of the formulae II to VII required for the preparation of the compounds of the formula I are known or they can easily be prepared by the processes known for the particular class of compound.

Examples of suitable starting compounds of the formula II are piperazin-1-yl-acetic acid amide, methylamide, ethylamide, isopropylamide, butylamide, dimethylamide, diethylamide, benzylamide, N-methylbenzylamide, morpholide, pyrrolidide, piperidide, N-methylpiperazide, cyclohexamethyleneimide, diethanolamide, (2-methoxy)-ethylamide, (2-ethoxy)-ethylamide, dipropanolamide, (3-methoxy)-propylamide, 2-methoxy-carbonyl-pyrrolidide, 2-aminocarbonyl-pyrrolidide, diethylaminoethylamide, dimethylaminopropylamide, methylaminoethylamide, 3,4-dimethoxyphenethylamide, 4-methoxybenzylamide, pyrid-3-yl-methylamide and pyrid-2-yl-methylamide. Where they are not already known, the starting compounds of the formula II can be prepared, for example, by reacting piperazine with a compound of the formula V, or by reacting a piperazin-1-yl-acetic acid alkyl ester of the formula VIII

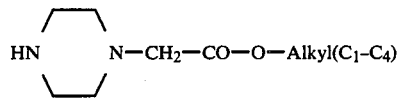

(VIII)

with an amine of the formula VII. These reactions are preferably carried out in one of the solvents already mentioned.

Examples of suitable acylating agents of the formula III are: benzoyl chloride, 2-, 3- or 4-methoxybenzoyl chloride, 2,3-, 2,4- or 3,4-dimethoxybenzoyl chloride, 2-, 3- or 4-chlorobenzoyl chloride, methyl nicotinate, 2- and 3-thenoyl chloride, 2- and 3-furoyl chloride, 4-chlorophenoxyacetyl chloride, 2-, 3- or 4-chlorophenyl isocyanate, isocyanic acid (potassium cyanate+mineral acid), benzoic acid, methyl benzoate, benzoic anhydride, isonicotinoyl chloride, methyl 4-hydroxy-3-methoxybenzoate, 3,4,5-trimethoxybenzoyl chloride, 3,4-dichlorobenzoyl chloride, 2-, 3- or 4-fluorobenzoyl chloride, 2-, 3- or 4-bromobenzoyl chloride, 4-tert.-butyl-benzoyl chloride, 4-methoxycarbonyl-benzoyl chloride, 4-dimethylamino-benzoyl chloride, methyl 2-, 3- or 4-methylmercaptobenzoate, methyl isocyanate, isopropyl isocyanate and methyl, ethyl, n-propyl, i-propyl, n-butyl, i-butyl, or tert.-butyl chloroformate. The acylating agents of the formula III can easily be synthesised by the processes known for the preparation of acid halides, in particular acid chlorides, carboxylic acid esters, carboxylic acid anhydrides, isocyanates and chloroformic acid esters.

Suitable piperazides of the formula IV can easily be prepared by reacting piperazine with an acylating agent IIIa, IIIb and IIIc by known processes. Examples of suitable piperazides of the formula IV are: the piperazides of benzoic acid, 2-, 3- or 4-methoxybenzoic acid, 2,3- or 3,4-dimethoxybenzoic acid, 2-, 3- or 4-chlorobenzoic acid, nicotinic acid, 2- or 3-thiophenecarboxylic acid, 2- or 3-furanecarboxylic acid, 4-chlorophenoxyacetic acid, isonicotinic acid, 3,4,5-trimethoxybenzoic acid, 3,4-dichlorobenzoic acid, 2-, 3- or 4-fluorobenzoic acid, 2-, 3- or 4-bromobenzoic acid, 2-, 3- or 4-chlorobenzoic acid, 4-tert.-butylbenzoic acid, 4-methoxycarbonylbenzoic acid, 4-dimethylaminobenzoic acid and 2-, 3- or 4-methylmercapto-benzoic acid; N-(aminocarbonyl)-piperazine, N-(methylaminocarbonyl)-piperazine, N-(ethylaminocarbonyl)-piperazine, N-(isopropylaminocarbonyl)-piperazine, N-(tert.-butylaminocarbonyl)-piperazine, N-(n-butylaminocarbonyl)-piperazine, N-(n-pentylaminocarbonyl)-piperazine, N-(isopentylaminocarbonyl)-piperazine, N-(methoxycarbonyl)-piperazine, N-(ethoxycarbonyl)-piperazine, N-(isopropoxycarbonyl)-piperazine, N-(n-propoxycarbonyl)-piperazine, N-(n-butoxycarbonyl)-piperazine and N-(isobutoxycarbonyl)-piperazine.

Examples of suitable starting compounds of the formula V are: chloro-, bromo-, mesyloxy-, phenylsulphonyloxy- or p-tosyloxy-acetic acid methylamide, ethylamide, n-propylamide, isopropylamide, n-butylamide, isobutylamide, dimethylamide, diethylamide, di-n-propylamide, di-n-butylamide, N-methyl-N-n-propylamide, benzylamide, methylbenzylamide, morpholide, pyrrolidide, piperidide, N-methyl-piperazide, cyclohexamethyleneimide, diethanolamide, 2-(methoxy)-ethylamide, 2-(ethoxy)-ethylamide, dipropanolamide, 3-(methoxy)-propylamide, 2-(methoxycarbonyl)-pyrrolidide, 2-aminocarbonyl-pyrrolidide, diethylaminoethylamide, dimethylaminopropylamide, methylaminoethylamide, 3,4-dimethoxyphenylethylamide, 4-methoxybenzylamide, pyrid-3-yl-methylamide and pyrid-2-yl-methylamide. The starting compounds of the formula V can be prepared, for example, by acylating an amine of the formula VII with chloroacetyl chloride by known processes.

Examples of suitable starting compounds of the formula VI are: methyl or ethyl 4-benzoyl-piperazin-1-yl-acetate, methyl or ethyl 4-(4-methoxybenzoyl)-piperazin-1-yl-acetate, methyl or ethyl 4-(2,3-, 2,4- or 3,4-dimethoxybenzoyl)-piperazin-1-yl-acetate, methyl or ethyl 4-(2-, 3- or 4-chlorobenzoyl)-piperazin-1-yl-acetate, methyl or ethyl 4-nicotinoyl-piperazin-1-yl-acetate, methyl or ethyl 4-(2- or 3-furoyl)-piperazin-1-yl-acetate, methyl or ethyl 4-(2- or 3-thenoyl)-piperazin-1-yl-acetate, methyl or ethyl 4-aminocarbonyl-piperazin-1-yl-acetate, methyl or ethyl 4-isopropylaminocarbonyl-piperazin-1-yl-acetate, methyl or ethyl 4-phenylaminocarbonyl-piperazin-1-yl-acetate, methyl or ethyl 4-(4-methoxyphenylaminocarbonyl)-piperazin-1-yl-acetate, 4-(2-, 3- or 4-fluorobenzoyl)-piperazin-1-yl-acetyl chloride, 4-(2-, 3- or 4-chlorobenzoyl)-piperazin-1-yl-acetyl chloride, 4-(2-, 3- or 4-dimethylaminobenzoyl)-piperazin-1-yl-acetyl chloride and 4-(2-, 3- or 4-methylmercapto)-piperazin-1-yl-acetyl chloride.

The starting compounds of the formula VI can be prepared, for example, by reacting a compound IV with a compound of the formula Hal—CH$_2$—CO—(C$_1$-C$_4$)—alkyl, wherein Hal denotes halogen, in particular chlorine, or by reacting an alkyl piperazin-1-yl-acetate of the formula VIII with an acylating agent IIIa, IIIb or IIIc.

The amines of the formula VII required as starting substances are known, or they can easily be prepared by processes which are known from the literature. Examples of amines of the formula VII are: ammonia, methylamine, ethylamine, n-propylamine, i-propylamine, n-butylamine, sec.-butylamine, i-butylamine, 2-(ethoxy)-ethylamine, 2-(methoxy)-ethylamine, benzylamine, 2-phenethylamine, morpholine, N-methylpiperazine, pyrrolidine, piperidine, diethylamine, di-n-propylamine, di-n-butylamine, N-methyl-N-ethylamine, N-methyl-N-n-butylamine, 2-(hydroxycarbonyl)-pyrrolidine, 2-(methoxycarbonyl)-pyrrolidine, 2-(ethoxycarbonyl)-pyrrolidine, 2-(n-propoxycarbonyl)-pyrrolidine, 2-(tert.-butoxycarbonyl)-pyrrolidine, 2-(aminocarbonyl)-pyrrolidine, 2-(methylaminocarbonyl)-pyrrolidine, 2-(n-butylaminocarbonyl)-pyrrolidine, 2-(dimethylaminocarbonyl)-pyrrolidine, 2-(dibutylaminocarbonyl)-pyrrolidine, 2-(2-, 3- or 4-methoxy)-phenethylamine, 2-(2-, 3- or 4-methyl)-phenethylamine, 2-(2-, 3- or 4-pyridyl)-ethylamine, 2-, 3- or 4-pyridylmethylamine and 3-(diethylamino)-propylamine.

The substituted piperazin-1-yl-acetic acid amides of the formula I form acid addition salts with inorganic or organic acids. Inorganic and organic acids are suitable for the formation of such acid addition salts. Examples of suitable acids are: hydrogen chloride, hydrogen bromide, naphthalene disulphonic acids, in particular naphthalene-1,5-disulphonic acid, and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared in the customary manner by combining the components, advantageously in a suitable solvent or diluent. In the synthesis of the compounds of the formula I, the acid addition salts may initially be obtained in the course of working up. If desired, the free compounds of the general formula I can be obtained from the acid addition salts in a known manner, for example by dissolving or suspending in water and rendering the solution or suspension alkaline, for example with sodium hydroxide solution, and subsequently filtering.

The compounds of the formula I according to the invention and their pharmacologically acceptable acid addition salts have useful pharmacological properties. On the basis of their encephalotropic action, they can be used as agents for improving cerebral functions, for example memory and learning capacity. They thus represent an enrichment of pharmacy, and can be used for the treatment and prevention of diseases in humans, in particular in combating and preventing cerebral insufficiency and in improving intellectual learning capacity.

The compounds of the formula I and their pharmacologically acceptable acid addition salts can therefore be administered to humans as medicines by themselves, as mixtures with one another or in the form of pharmaceutical formulations which permit enteral or parenteral use and contain, as the active constituent, an effective dose of at least one compound of the formula I or of an acid addition salt thereof, in addition to customary pharmaceutically acceptable excipients and additives. The formulations usually contain about 0.5 to 90% by weight of the therapeutically active compound.

The medicines can be administered orally, for example in the form of pills, tablets, lacquered tablets, coated tablets, granules, hard and soft gelatin capsules, solutions, syrups, emulsions or suspensions or aerosol mixtures. However, administration can also be rectal, for example in the form of suppositories, or parenteral, for example in the form of injection solutions, or percutaneously, for example in the form of ointments or tinctures.

The pharmaceutical products are prepared in a manner which is known per se, pharmaceutically inert inorganic or organic excipients being used. For example, lactose, maize starch or derivatives thereof, talc, stearic acid or salts thereof and the like can be used for the preparation of pills, tablets, coated tablets and hard gelatin capsules. Examples of excipients for soft gelatin capsules and suppositories are fats, waxes, semi-solid and liquid polyols, natural or hardened oils and the like. Examples of suitable excipients for the preparation of solutions and syrups are water, sucrose, invert sugar, glucose, polyols and the like. Examples of suitable excipients for the preparation of injection solutions are water, alcohols, glycerol, polyols, vegetable oils and the like.

Besides the active compounds and excipients, the pharmaceutical products can also contain additives, such as, for example, fillers, extenders, disintegrating agents, binders, lubricants, wetting agents, stabilisers, emulsifiers, preservatives, sweeteners, colorants, flavouring agents, aromatising agents, thickeners, diluents and buffer substances, and furthermore solvents or solubilising agents or agents to achieve a depot effect, as well as salts for modifying the osmotic pressure, coating agents or antioxidants. They can also contain two or more compounds of the formula I or their pharmacologically acceptable acid addition salts, as well as other therapeutically active substances.

Examples of such other therapeutically active substances are: β-receptor blockers, such as, for example, propranolol, pindolol and metoprolol; antianginal agents, such as, for example, carbocromen; molsidomin; sedatives such as, for example, barbituric acid derivatives, 1,4-benzodiazepines and meprobamate; diuretics, such as, for example, chlorothiazide; agents which tonisise the heart, such as, for example, digitalis products; hypotensive agents, such as, for example, hydralazine, dihydralazine and prazosin; clonidine and Rauwolfia alkaloids; agents which reduce the level of fatty acids in the blood, such as, for example, bezafibrate and fenofibrate; and agents for the prophylaxis of thromboses, such as, for example, phenprocoumon.

The compounds of the formula I and their pharmacologically acceptable acid addition salts and pharmaceutical products which contain the compounds of the formula I or their pharmacologically acceptable acid addition salts as the active compound can be used in combating or preventing diseases in humans, in particular in combating or preventing cerebral insufficiency and in improving intellectual learning capacity. The dosage can vary within wide limits and is to be adapted to the individual circumstances in each particular case. In general, a daily dose of about 1 to 1,000 mg/kg, preferably 5 to 800 mg/kg, of body weight is appropriate to achieve effective results on oral administration, whilst on intravenous administration, the daily dose is in general about 5 to 500 mg/kg, preferably 5 to 250 mg/kg, of body weight. The daily dose is usually divided into several, for example 2, 3 or 4, part administrations, especially when relatively large amounts are administered. If appropriate, depending on the individual behaviour, it may prove necessary to deviate upwards or downwards from the daily dose stated.

Encephalotropic action of the compounds according to the invention was tested, for example, by the passive avoidance test, which is carried out as follows: the test apparatus is a light dark box with a grid floor which can be electrified in the dark section.

90 minutes after administration of a control or product injection, inexperienced male mice are treated with scopolamine hydrobromide (3 mg/kg, subcutaneously). 5 minutes later, the mice are placed in the light section of the box. After being changed to the dark section of the box, they receive an electric shock, unpleasant to them, through their feet. After 24 hours, each mouse is placed once in the light section of the test apparatus and the residence time (maximum 180 seconds) is measured. The significant action of the test substance in comparison with the control group is calculated by means of the median test.

The minimum effective dose MED of a product is designated as that dose which displays a significant action against scopolamine. The animals treated with an active dose of a product and scopolamine show a long residence time, as do the animals which are not treated with scopolamine, whilst those treated with a control injection and scopolamine show a short residence time. For comparison, the MED of piracetam was also determined. During testing, the values given in the table which follows are obtained:

| Compound according to the following examples | MED in mg/kg per orally |
|---|---|
| 1, 3, 5 | 3 |
| 7, 13, 28 | less than 30 |
| 2, 8, 10, 11, 12, 13, 16, 17, 27, 29, 30 | 30 |
| | 30 |
| Piracetam (comparison) | 100 |

EXAMPLE 1

4-(4-Methoxybenzoyl)-piperazin-1-yl-acetic acid morpholide hydrochloride 10.25 g of piperazin-1-yl-acetic acid morpholide are cooled to 0° C. in 20 ml of methylene chloride. 8.75 g of anisoyl chloride are added dropwise in the course of 15 minutes. After the mixture has been subsequently stirred for 4 hours, it is diluted with isopropanol, whereupon the colourless product precipitates. It is filtered off with suction and dried.

Yield: 14.6.

Melting point: 176°–178° C.

Elemental analysis: Calculated: C 56.3, H 6.8, Cl 9.3, N 10.9, O 16.7. Found: C 56.1, H 6.6, Cl 9.5, N 10.6, O 17.0.

EXAMPLE 2

4-Aminocarbonyl-piperazin-1-yl-acetic acid morpholide 9.1 g of piperazin-1-yl-acetic acid morpholide are dissolved in 30 ml of water and 4.4 ml of concentrated hydrochloric acid and the solution is cooled to 20° C. A solution of 3.1 g of potassium cyanate in 15 ml of water is slowly added dropwise, with cooling. A further 4.4 ml of concentrated hydrochloric acid are then added and the mixture is left to stand overnight at 20° C. The solution is rendered neutral with 2N sodium hydroxide solution and concentrated. Boiling up of the solid residue with isopropanol and cooling of the solution gives 5.3 g of colourless crystals, which are recrystallised from ethanol.

Melting point: 165° C.

Elemental analysis: Calculated: C 51.6, H 7.8, N 21.9, O 18.8. Found: C 51.3, H 7.6, H 22.7, O 18.6.

EXAMPLE 3

4-(4-Methoxybenzoyl)-piperazin-1-yl-acetic acid pyrrolidide hydrochloride 9.4 g of piperazin-1-yl-acetic acid pyrrolidide are dissolved in 10 ml of methylene chloride. A solution of 8.75 g of anisic acid chloride in 10 ml of methylene chloride is added dropwise at 0°. After the mixture had been stirred at 25° C. for 60 minutes, the crystals are filtered off with suction and dried in vacuo.

Yield: 10.7 g.
Melting point: 245° C.
Elemental analysis: Calculated: C 58.8, H 7.1, N 11.4, O 13.1, Cl 9.7. Found: C 58.5, H 7.0, N 11.1, O 13.5, Cl 10.0.

EXAMPLE 4

4-(4-Methoxybenzoyl)-piperazin-1-yl-acetic acid 2-(aminocarbonyl)-pyrrolidide (a) 6 g of chloroacetic acid 2-(aminocarbonyl)-pyrrolidide, 7 g of 4-anisoyl-piperazine and 4.4 g of potassium carbonate are stirred at 50° C. in 50 ml of dimethylformamide for 2 hours. The reaction mixture is concentrated and the residue is taken up in 100 ml of water. Potassium carbonate is added to the aqueous solution and the mixture is extracted several times by shaking with methylene chloride. After drying and concentration, the organic phase gives an oily residue, which solidifies on trituration with ethyl acetate. The solid is filtered off with suction and rinsed with ethyl acetate.

Melting point: 149°–150° C.
Analysis: Calculated: C 61.0, H 7.0, N 15.0, O 17.1. Found: C 60.9, H 7.0, N 15.2, O 17.0.

(b) The chloroacetic acid 2-(aminocarbonyl)-pyrrolidide required as the starting substance is prepared as follows:

11.4 g of proline amide and 10.1 g of triethylamine are dissolved in 100 ml of methylene chloride. 11.3 g of chloroacetyl chloride are added dropwise at 30° C. and the mixture is then stirred at room temperature for 6 hours. After concentration in vacuo, the residue is dissolved in 150 ml of water and the resulting mixture is extracted by shaking with 2×100 ml of methylene chloride. The organic phase is dried over Na2SO4 and the methylene chloride is removed in a rotary evaporator. The residue is recrystallised from isopropanol.

Melting point: 136°–137° C.
Analysis: Calculated: C 44.1, H 5.8, Cl 18.6, N 14.7, O 16.8. Found: C 44.0, H 5.6, Cl 18.5, N 15.0, O 16.8.

EXAMPLE 5

4-(4-Methoxybenzoyl)-piperazin-1-yl-acetic acid morpholide

A solution of 15.4 g of chloroacetic acid morpholide in 50 ml of toluene is added dropwise to a mixture of 22 g of N-(4-methoxybenzoyl)-piperazine, 15.2 g of potassium carbonate and 200 mL of toluene at room temperature. The mixture is then heated under reflux for 6 hours, with stirring, and is filtered hot. Colourless crystals precipitate from the filtrate on cooling.

Yield: 23.5 g.
Melting point: 148°–149° C.
Elemental analysis: Calculated C 62.2, H 7.3, N 12.1, O 18.4. Found: C 62.0, H 7.2, N 12.2, O 18.3.

The N-(4-methoxybenzoyl)-piperazine used as a starting substance was obtained as a viscous oil by reacting 1 mol of piperazine with 0.5 mol of anisic acid chloride in glacial acetic acid. The chloroacetic acid morpholide used as a starting substance was obtained as a colourless oil by reacting 2 mol of morpholine with 1 mol of chloroacetyl chloride in toluene.

EXAMPLE 6

4-(4-Chlorobenzoyl)-piperazin-1-yl-acetic acid morpholide hydrochloride 5 g of piperazinoacetic acid morpholide and 4.2 g of chlorobenzoyl chloride are brought together in 50 ml of methylene chloride at 0° C. The mixture is stirred at room temperature for 2 hours and cooled again to 0° C., whereupon a precipitate separates out, and is recrystallised from isopropanol.

Yield: 7.6 g.
Melting point: 236°–238° C.
Calculated: C 52.5, H 5.9, N 10.8, O 12.4, Cl 18.3. Found: C 52.5, H 5.9, N 10.6, O 12.6, Cl 18.6.

EXAMPLE 7

4-(4-Methoxybenzoyl)-piperazin-1-yl-acetic acid isopropylamide hydrochloride A solution of 4.6 g of anisic acid chloride in 20 ml of methylene chloride is added dropwise to 5 g of piperazinoacetic acid isopropylamide in 20 ml of methylene chloride at 0° C. The mixture is then stirred at room temperature for 4 hours and subsequently concentrated. The residue is recrystallised from isopropanol.

Yield: 7.5 g.
Melting point: 227°–230° C.
Calculated: C 57.4, H 7.3, N 11.8, O 13.5, Cl 10.0. Found: C 57.6, H 7.3, N 11.9, O 13.2, Cl 10.3.

The following compounds can be prepared in a manner similar to that described in Examples 1 to 7:

| Example | | Melting point: °C. |
|---|---|---|
| 8 | 4-Benzoyl-piperazin-1-yl-acetic acid | 204–206 |
| 9 | 4-(4-Methylbenzoyl)-piperazin-1-yl-acetic acid methylamide | 178–179 |
| 10 | 4-nicotinoyl-piperazin-1-yl-acetic acid dibutylamide | 89–91 |
| 11 | 4-(4-Acetoxy-3-methoxybenzoyl)-piperazin-1-yl-acetic acid dimethylamide | 167–168 |
| 12 | 4-(3,4-Dimethoxybenzoyl)-piperazin-1-yl-acetic acid 2-methoxyethylamide | 163–164 |
| 13 | 4-(3-Chlorophenylaminocarbonyl)-piperazin-1-yl-acetic acid piperidide | 177–180 |
| 14 | 4-(4-Chlorobenzoyl)-piperazin-1-yl-acetic acid 2-(diethylamino)-ethylamide | 102–104 |
| 15 | 4-Ethoxycarbonyl-piperazin-1-yl-acetic acid benzylamide | 131–132 |
| 16 | 4-(4-Chlorophenoxyacetyl)-piperazin-1-yl-acetic acid N—methylpiperazide | 101–102 |
| 17 | 4-(3,4,5-Trimethoxybenzoyl)-piperazin-1-yl-acetic acid 2-(3,4-dimethoxyphenyl)-ethylamide | 201–203 |
| 18 | 4-(3,4-Dichlorobenzoyl)-piperazin-1-yl-acetic acid 4-methoxybenzylamide | 199–200 |
| 19 | 4-(4-Methoxybenzoyl)-piperazin-1-yl-acetic acid diethanolamide | oil |
| 20 | 4-(4-Methoxybenzoyl)-piperazin-1-yl-acetic acid 2-(ethylaminocarbonyl)-pyrrolidide | oil |
| 21 | 4-(4-Fluorobenzoyl)-piperazin-1-yl-acetic acid 2-(methylaminocarbonyl)-pyrrolidide | 98–101 |
| 22 | 4-(3-Bromobenzoyl)-piperazin-1-yl-acetic acid isopropylamide | 213–215 |
| 23 | 4-(4-tert.-Butylbenzoyl)-piperazin-1-yl-acetic acid isopropylamide | 187–189 |
| 24 | 4-(4-Methoxycarbonylbenzoyl)-piperazin-1-yl-acetic acid (2-hydroxyethyl)-amide | 147–149 |
| 25 | 4-(2-Furoyl)-piperazin-1-yl-acetic acid (3-methoxypropyl)-amide | 150–152 |

-continued

| Example | | Melting point: °C. |
|---|---|---|
| 26 | 4-(4-Chlorobenzoyl)-piperazin-1-yl-acetic acid morpholide hydrochloride | 235–238 |
| 27 | 4-(Benzoyl)-piperazin-1-yl-acetic acid morpholide | 135–137 |
| 28 | 4-(3-Chlorophenylaminocarbonyl)-piperazin-1-yl-acetic acid morpholide | 155–157 |
| 29 | 4-(3-Methoxy-4-acetoxybenzoyl)-piperazin-1-yl-acetic acid morpholide hydrochloride | Decomposition from 70° C. |
| 30 | 4-(4-Methoxybenzoyl)-piperazin-1-yl-acetic acid (2-methoxycarbonyl)-pyrrolidide | 87–89 |
| 31 | 4-(2-Thenoyl)-piperazin-1-yl-acetic acid (2-pyridylmethyl)-amide | 135–137 |

Pharmaceutical products are described in the following examples, where a different active compound according to the invention can be used instead of the 4-(methoxybenzoyl)-piperazin-1-yl-acetic acid morpholide used as the active compound.

EXAMPLE 32

Soft gelatin capsules containing 40 mg of active compound per capsule:

| | per capsule |
|---|---|
| 4-(Methoxybenzoyl)-piperazin-1-yl-acetic acid morpholide | 40 mg |
| Triglyceride mixture fractionated from coconut oil | 150 mg |
| Capsule contents | 190 mg |

EXAMPLE 33

Injection solution containing 10 mg of active compound per ml:

| | per ml |
|---|---|
| 4-(Methoxybenzoyl)-piperazin-1-yl-acetic acid morpholide | 10 mg |
| Sodium chloride | 2.7 mg |
| Water for injection purposes | to 1.0 ml |

EXAMPLE 34

Emulsion containing 25 mg of active compound per 5 ml:

| per 100 ml | |
|---|---|
| 4-(Methoxybenzoyl)-piperazin-1-yl-acetic acid morpholide | 0.5 g |
| Neutral oil | q.s. |
| Polyoxyethylene stearate | q.s. |
| Pure glycerol | 0.2 to 2.0 g |
| Flavouring | q.s. |
| Water (demineralised or distilled) | to 100 ml |

EXAMPLE 35

Rectal medicament form containing 15 mg of active compound per suppository:

| | per suppository |
|---|---|
| 4-(Methoxybenzoyl)-piperazin-1-yl-acetic acid morpholide | 15 mg |
| Suppository base | to 2 g |

EXAMPLE 36

Tablets containing 30 mg of active compound per tablet:

| per tablet | |
|---|---|
| 4-(Methoxybenzoyl)-piperazin-1-yl-acetic acid morpholide | 30 mg |
| Lactate (finely ground) | 5 mg |
| Maize starch (white) | 150 mg |
| Lactose | 60 mg |
| Microcrystalline cellulose | 50 mg |
| Polyvinyl pyrrolidone | 20 mg |
| Magnesium stearate | 2 mg |
| Sodium carboxymethyl-starch | 25 mg |
| | 342 mg |

EXAMPLE 37

Coated tablets containing an active compound according to the invention and another therapeutically active substance:

| 4-(Methoxybenzoyl)-piperazin-1-yl-acetic acid morpholide | 30 mg |
|---|---|
| Propranolol | 40 mg |
| Lactose | 90 mg |
| Maize starch | 90 mg |
| Secondary calcium phosphate | 34 mg |
| Soluble starch | 3 mg |
| Magnesium stearate | 3 mg |
| Colloidal silicic acid | 4 mg |
| | 294 mg |

EXAMPLE 38

Coated tablets containing an active compound according to the invention and another therapeutically active substance:

| 4-(Methoxybenzoyl)-piperazin-1-yl-acetic acid morpholide | 25 mg |
|---|---|
| Molsidomine | 5 mg |
| Lactose | 60 mg |
| Maize starch | 90 mg |
| Secondary calcium phosphate | 30 mg |
| Soluble starch | 3 mg |
| Magnesium stearate | 3 mg |
| Colloidal silicic acid | 4 mg |
| | 220 mg |

EXAMPLE 39

Capsules containing an active compound according to the invention and another therapeutically active substance:

| 4-(Methoxybenzoyl)-piperazin-1-yl-acetic acid morpholide | 20 mg |
|---|---|
| Prazosin | 5 mg |
| Maize starch | 185 mg |
| | 210 mg |

What is claimed is:

1. A piperazin-1-yl-acetic acid amide of the formula I

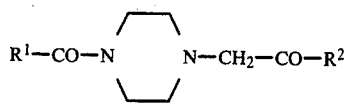 (I)

wherein $R^1$ denotes phenyl, phenyl which is substituted by one, two or three independent substituents from the group comprising $(C_1-C_4)$—alkyl, —O—$(C_1-C_4)$—alkyl, acetoxy, —CO—O-$(C_1-C_4)$—alkyl, —$SCH_3$, —$NH_2$, —NH—$(C_1-C_3)$—alkyl, —N$((C_1-C_2)$—alkyl$)_2$, —F, —Cl, —Br, —I, —OH, and —SH, or pyridyl, thienyl, furyl, chlorophenoxymethyl, amino, alkylamino with 1 to 5 C atoms, phenylamino, phenylamino which is substituted in the phenyl nucleus by —Cl, —Br, —$CH_3$, or —$OCH_3$, or alkoxy with 1 to 4 C-atoms, $R^2$ denotes amino, alkylamino with 1 to 4 C atoms, dialkylamino with 1 to 4 C atoms in each alkyl radical, morpholino, 4-methyl-piperazin-1-yl, pyrrolidin-1-yl, piperidino, cyclohexamethyleneimino, diethanolamino, dipropanolamino, —NH$(CH_2)_n$-$R^3$, —NH$(CH_2)_m$—$R^4$ or 2-$(R^3$—carbonyl)-pyrrolidin-1-yl, $R^3$ denotes hydroxyl, alkoxy with 1 to 4 C atoms or dialkylamino with 1 to 4 C atoms in each alkyl radical, $R^4$ denotes phenyl, methoxyphenyl, methylphenyl, dimethoxyphenyl, dimethylphenyl or pyridyl, n denotes 2 or 3 and m denotes 1 or 2, and their pharmacologically-acceptable acid-addition salts, with the restriction, that in cases in which $R^1$ denotes a phenyl radical substituted by Cl, said phenyl radical cannot have a further substituent selected from the group —OH and O—alkyl($C_1-C_4$).

2. A piperazin-1-yl-acetic acid amide according to claim 1, wherein $R^1$ denotes phenyl, methoxyphenyl, chlorophenyl, bromophenyl, fluorophenyl, $(C_1-C_4)$—alkylphenyl, 4-chlorophenoxymetyl, dimethoxyphenyl, dichlorophenyl, methoxycarbonyl-phenyl, acetoxy-methoxyphenyl, $(C_1-C_2)$-alkoxy, trimethoxyphenyl, thienyl, pyridyl or furyl.

3. A substituted piperazin-1-yl-acetic acid amide according to claim 1, wherein $R^2$ denotes amino, $(C_1-C_4)$-alkylamino, di-$(C_1-C_4)$-alkyl-1 amino, morpholino, [4-methylpiper-azin-1-yl] 4-methylpiperazin-1-yl, pyrrolidin-1-yl, piperidino, diethanolamino, —NH$(CH_2)_n$—$R^3$, —NH$(CH_2)_m$—$R^4$ or 2-$(R^3$—carbonyl)-pyrrolidin-1-yl.

4. A piperazin-1-yl-acetic acid amide according to claim 1, wherein $R^3$ denotes hydroxyl, alkoxy with 1 or 2 C atoms, amino, alkylamino with 1 or 2 C atoms or dialkylamino with 1 or 2 C atoms in each alkyl radical.

5. A piperazin-1-yl-acetic acid amide according to claim 1, wherein $R^4$ denotes phenyl, methoxyphenyl or dimethoxyphenyl.

6. A Substituted piperazin-1-yl-acetic acid amide of the formula I

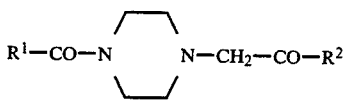 (I)

wherein $R^1$ denotes phenyl, methoxyphenyl, chlorophenyl, bromophenyl, fluorophenyl, $(C_1-C_4)$-alkylphenyl, 4-chlorophenoxymethyl, dimethoxyphenyl, dichlorophenyl, methoxycarbonyl-phenyl, acetoxy-methoxyphenyl, $(C_1-C_4)$-alkoxy, trimethoxyphenyl, thienyl, pyridyl or furyl, $R^2$ denotes amino, $(C_1-C_4)$-alkylamino, di-$(C_1-C_4)$-alkylamino, morpholino, [4-methylpiperazin-1-yl] 4-methylpiperazin-1-yl, pyrrolidin-1-yl, piperidino, diethanolamino, —NH$(CH_2)_n$-$R^3$, —NH$(CH_2)_m$—$R^4$ or 2-$(R^3$—carbonyl)-pyrrolidin-1-yl, $R^3$ denotes hydroxyl, alkoxy with 1 or 2 C atoms, amino, alkylamino with 1 or 2 C atoms or dialkyl-amino with 1 or 2 C atoms in each alkyl radical and $R^4$ denotes phenyl, methoxyphenyl or dimethoxyphenyl, n denotes 2 or 3 and m denotes 1 or 2, and their pharmacologically-acceptable acid-addition salts.

7. 4-(4-Methoxybenzoyl)-piperazin-1-yl-acetic acid morpholide or a pharmacologically acceptable acid addition salt thereof.

8. A process for treatment of cerebral insufficiency or improving intellectual performance which comprises administering an effective amount of a compound according to claim 1 to a subject afflicted with such illness.

9. A medicament composition which is useful for treatment of cerebral insufficiency or improving intellectual performance and which comprises a pharmaceutically-acceptable excipient and/or additive and an effective amount, per unit dose, of a compound according to claim 1.

* * * * *